United States Patent [19]

Schumacher et al.

[11] Patent Number: 5,080,709

[45] Date of Patent: Jan. 14, 1992

[54] HERBICIDAL AGENTS CONTAINING CHLOROBENZOXAZOLYL-PHENOXY PROPIONIC ACID ESTERS AND EITHER BROMOXYNIL OR IOXYNIL

[75] Inventors: Hans Schumacher, Flörsheim am Main; Rudolf Heinrich, Kelkheim (Taunus); Hans-Günter Marks, Hattersheim am Main, all of Fed. Rep. of Germany

[73] Assignee: Hoechst Aktiengesellschaft, Frankfurt, Fed. Rep. of Germany

[21] Appl. No.: 506,509

[22] Filed: Apr. 5, 1990

Related U.S. Application Data

[63] Continuation of Ser. No. 308,978, Feb. 8, 1989, abandoned, which is a continuation of Ser. No. 67,430, Jun. 25, 1987, abandoned, which is a continuation of Ser. No. 672,583, Nov. 16, 1984, abandoned.

[30] Foreign Application Priority Data

Nov. 9, 1983 [DE] Fed. Rep. of Germany ...... 3341884
Apr. 21, 1984 [DE] Fed. Rep. of Germany ...... 3415069

[51] Int. Cl.$^5$ .................... A01N 43/76; A01N 37/34
[52] U.S. Cl. .................................... 71/88; 71/105
[58] Field of Search .......................... 71/105, 88

[56] References Cited

U.S. PATENT DOCUMENTS 3,397,054 8/1968 Hart et al. .......................... 71/105
4,332,961 6/1982 Takahashi et al. ................. 71/88
4,531,969 7/1985 Nestler et al. ..................... 71/88

FOREIGN PATENT DOCUMENTS 2011787 7/1979 United Kingdom ............... 71/105

OTHER PUBLICATIONS

Schumacher et al. (II), "Herbicide Mixtures", CA:91:187961h, 1979.
Hoechst, "Herbicidal Composition", CA 92:175774g, 1980.
Ebdon et al., "Chemical Control of Spurge, etc.", CA 96:157220b, 1982.
Allen et al., "Wild Oat Control in etc.", CA 86:84642x, 1977.
O'Sullivan et al., "Interaction Between, etc.", CA 90:98444d, 1979.
The Pesticide Manual, 7th Edition, The British Crop Protection Council, pp. 770, 3960, 7790, 7860, 8020, 9534.

*Primary Examiner*—Glennon H. Hollrah
*Assistant Examiner*—Brian G. Bembenick

[57] ABSTRACT

The herbicidal agents containing a compound of the formula (A)

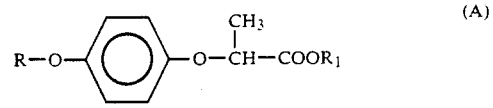

in which R denotes

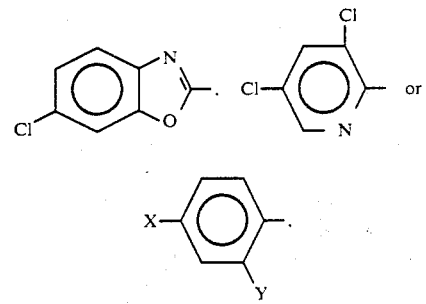

in which X denotes chlorine or bromine and Y denotes H or chlorine, and $R_1$ denotes H, alkyl, alkinyl or one equivalent of a cation, in combination with a compound of the formula (B)

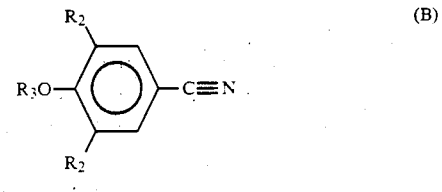

in which $R_2$ denotes bromine or iodine and $R_3$ denotes H, $NH_4$, an alkali metal cation or $(C_1-C_8)$-alkyl, or with a compound of the formula (C)

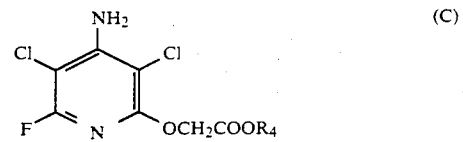

in which $R_4$ denotes H, $(C_1-C_8)$-alkyl or one equivalent of a cation, with the condition that if, in formula (A), R denotes

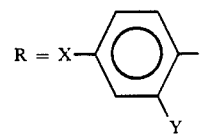

combinations of the compound of the formula (A) with compounds of the formula (B) are excluded.

15 Claims, No Drawings

HERBICIDAL AGENTS CONTAINING CHLOROBENZOXAZOLYL-PHENOXY PROPIONIC ACID ESTERS AND EITHER BROMOXYNIL OR IOXYNIL

This application is a continuation of application Ser. No. 308,978, filed Feb. 8, 1989 (now abandoned), which in turn is a continuation of Ser. No. 067,430 filed June 25, 1987 (now abandoned), which in turn is a continuation of Ser. No. 672,583, filed Nov. 16, 1984 (now abandoned).

The present invention relates to herbicidal agents containing a compound of the formula (A)

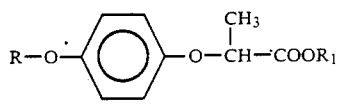

in which
R denotes

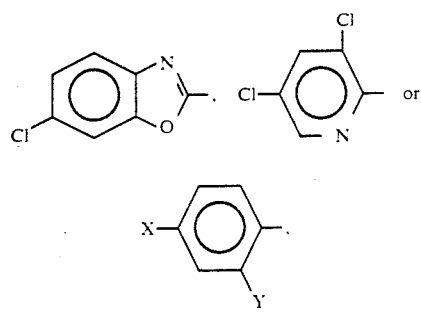

in which
X denotes chlorine or bromine and Y denotes H or chlorine, and
$R_1$ = H, $(C_1-C_4)$-alkyl, $(C_2-C_4)$-alkinyl or one equivalent of a cation, in combination with a compound of the formula (B)

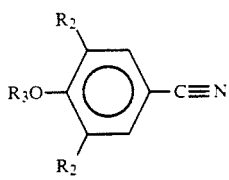

in which
$R_2$ denotes bromine or iodine and
$R_3$ denotes H, $NH_4$, an alkali metal cation or $(C_1-C_8)$-alkyl,
or with a compound of the formula (C)

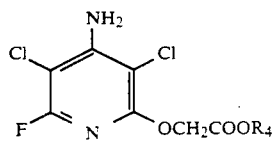

in which
$R_4$ denotes H, $(C_1-C_8)$-alkyl or one equivalent of a cation, with the condition that if, in formula (A)

R denotes 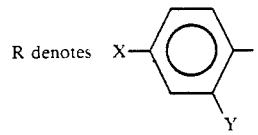

combinations of the compounds of the formula (A) with compounds of the formula (B) are excluded.

By one equivalent of a cation there is to be understood, in each case, one equivalent of a metal cation, such as, for example, an alkali metal or alkaline earth metal cation, or of an optionally $(C_1-C_4)$-alkyl-substituted ammonium ion.

Since the compounds of the formula (A) have a center of asymmetry in the propionic acid part, they can be in the form of pure sterioisomers or in the form of sterioisomer mixtures.

The compounds of the formula (A) are particularly active against monocotyledonous harmful plants, such as, for example, *Alopecurus myosuroides* and *Avena fatua* (c.f. German Offenlegungsschrift 2,640,730 and German Offenlengungsschrift 2,223,894).

$R_1$ particularly denotes $(C_1-C_2)$-alkyl. Compounds of the formula (A) which are of particular interest are ethyl α-[4-(6-chlorobenzoxazolyloxy)-phenoxy]-propionate ($A_1$), methyl α-[4-(2,4-dichlorophenoxy)-phenoxy]-propionate ($A_2$) (common name: diclofop-methyl) and prop-2-inyl α-[4-(3,5-dichloro-pyrid-2-yloxy)-phenoxy]-propionate, and components ($A_1$) and ($A_2$) are particularly preferred.

Preferred compounds of the formula (B) are those where $R_3$=octanoyl, common names: bromoxynil octanoyl ester for $R_2$=bromine (compound $B_1$) and ioxynil octyl ester for $R_2$=iodine (compound $B_2$). Both compounds are known as agents for combating weeds in cereals from Dutch Offenlegungsschrift 6,411,452.

The preferred compound of the formula (C) is that in which $R_4$=octyl ($C_1$). This compound is described in Weed Research Organization, Technical Report No. 63.

The compounds of the formulae (B) and (C) are distinguished by a good activity against dicotyledonous harmful plants, such as *Stellaria media* and *Chenopodium album*.

Surprisingly striking synergistic effects were found when the compounds of the formula (A) were combined with compounds of the formula (B) or (C).

The active substance combinations according to the invention can be used for combating undesirable species of plants, such as, for example, *Alopecurus myosuroides, Avena fatua, Stellaria media, Chenopodium album, Setaria viridis*, Phalaris sp., *Galium aparine*, Matricaria sp., *Sinapis arvense* and *Miosotis arvense* in crops of useful plants, in particular in cereal crops, such as wheat and barley, preferably wheat.

The mixing ratios of the components of the formulae (A) and (B) or (C) can vary within wide limits. Thus, the ratio of components A to B (or C) is in the range from 1:10 to 15:1; the range from 1:5 to 5:1 is preferred if R in formula (A) denotes 6-chlorobenzoxazolyl, and the range from 1:1 to 10:1 is preferred if R in formula (A) denotes

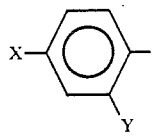

The combinations according to the invention can be used as tank mixes, in which the individual active substance components are mixed with one another only directly before application, or as finished formulations. As finished mixtures, they can be formulated, for example, in the form of wettable powders, emulsifiable concentrates, solutions, dispersions, dusting agents or granules, and then contain, if appropriate, the customary formulation auxiliaries, such as wetting agents, tackifiers, emulsifiers, dispersing agents, solid or liquid inert substances, grinding auxiliaries and solvents.

Wettable powders are products which are uniformly dispersable in water and which, in addition to the active substance and apart from diluents or inert substances, if appropriate, can also contain wetting agents, for example polyoxyethylated alkylphenols, polyoxyethylated oleylamines or stearylamines or alkyl- or alkylphenyl-sulfonates, and dispersing agents, for example sodium ligninsulfonate, sodium 2,2'-dinaphthyl-methane-6,6'-disulfonate, sodium dibutylnaphthalene sulfonate or sodium oleylmethyl-tauride.

Emulsifiable concentrates can be prepared, for example, by dissolving the active substance in an organic solvent, for example butanol, cyclohexanone, dimethylformamide, xylene, isophorone or higher-boiling aromatics, with the addition of one or more emulsifiers. Examples of emulsifiers which can be used are: calcium alkylarylsulfonates, fatty acid polyglycol esters, alkylaryl polyglycol ethers, fatty alcohol polyglycol ethers, polyoxyethylated oleylamines or stearylamines, propylene oxide/ethylene oxide condensation products, alkyl polyethers, sorbitan fatty acid esters, alkylaryl/propylene oxide/ethylene oxide condensation products and the like.

Dusting agents are obtained by grinding the active substance with finely divided, solid substances, for example talc or naturally occurring clays, such as kaolin, bentonite, pyrophillite or diatomaceous earth.

Granules can be prepared either by spraying a solution of the active substance onto an adsorbent granular inert material, or by applying active substance concentrates to the surface of carriers, such as sand or kaolinites, or a granular inert material by means of a binder, for example polyvinyl alcohol, sodium acrylate, methylhydroxyethyl cellulose or mineral oils. Suitable formulations of active substance can also be prepared in the manner customary for the preparation of fertilizer granules—if desired as a mixture with fertilizers.

The synergistic active substance mixtures according to the invention of compounds of the formulae A and B or C can be formulated in the form of usual formulations, in particular as wettable powders, emulsifiable concentrates, solutions, dispersions, dusting agents or granules. The total content of active substance in the multiple formulations is then about 2 to 95% by weight, preferably 10 to 70% by weight, the remainder to make up to 100% by weight consisting of the usual formulation auxiliaries, such as tackifiers, wetting agents, emulsifiers, dispersing agents, fillers, solvents and carriers.

The total concentration of active substance in wettable powders varies in the range from about 10 to 80% by weight.

In emulsifiable concentrates, the total concentration of active substance is in the range from about 10 to 70% by weight. In granules, it is about 2 to 10% by weight. Dust-like formulations contain about 5 to 20% by weight of active substance mixture.

The invention thus also relates to herbicidal agents containing 2 to 95% by weight, preferably 10 to 70% by weight, of an active substance combination of compounds of the formulae A and B or C, the remainder to make up to 100% by weight consisting of the usual formulation auxiliaries.

For use, the concentrates mentioned are diluted, if appropriate, in the customary manner, for example by means of water in the case of wettable powders, emulsifiable concentrates and dispersions. Dust-like and granular formulations and solutions which can be sprayed are in general not further diluted with additional inert substances before use. The application amount of the agents according to the invention also varies according to external conditions, such as temperature, humidity and the like. It can vary within wide limits, and is in general between 0.2 and 10 kg of active substance combination/ha, preferably 0.3–2.0 kg/ha.

The invention is illustrated by the following examples.

FORMULATION EXAMPLES

General Instructions

An active substance was dissolved in the solvent mixture in question at 50°–60° C., and the second active substance, if appropriate in the form of a melt, was then added. The individual emulsifiable components were added, with thorough stirring, and the mixture was allowed to cool. The resulting emulsifiable concentrates are slightly to moderately brown-colored.

The active substances and formulation auxiliaries shown in Examples 1–12 of the following Table are mixed with one another by this procedure. The numerical data in the Table correspond to parts by weight.

| Constituents of the formulations | 1 | 2 | 3 | 4 | 5 | 6 | 7 | 8 | 9 | 10 | 11 | 12 |
|---|---|---|---|---|---|---|---|---|---|---|---|---|
| Active substance (A$_1$), techn. | 10.1 | 3.6 | 16.6 | 10.1 | 3.6 | 16.6 | 10.1 | 3.6 | 16.6 | | | |
| Bromoxynil octyl ester (B$_1$), techn. | 14.3 | 22.5 | 5.1 | | | | | | | | | |
| Ioxynil octyl ester (B$_2$), techn. | | | | 13.5 | 22.2 | 4.7 | | | | | | |
| Active substance (C$_1$), techn. | | | | | | | 13.8 | 22.7 | 4.9 | 12.0 | 5.0 | 2.5 |
| Diclofop-methyl (A$_2$), techn. | | | | | | | | | | 12.0 | 25.0 | 25.0 |
| Xylene | 33.0 | 42.3 | 36.3 | 34.0 | 32.3 | 36.7 | 28.1 | 28.7 | 33.5 | 42.0 | 50.0 | 50.0 |
| Isophorone | | | | | 15.0 | | | 15.0 | | 20.0 | | |
| Cyclohexanone | | 5.6 | | 15.4 | | 20.0 | | | | | 10.0 | 10.0 |
| Dimethylformamide | 15.6 | | 1.50 | | | 15.0 | | | 15.0 | | | |
| Calcium dodecylbenzenesulfonate | 6.0 | 5.0 | 5.0 | 7.0 | 7.0 | 5.0 | 5.0 | 5.0 | 5.0 | 4.0 | 5.0 | 4.0 |

-continued

| Constituents of the formulations | Example No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Ethoxylated castor oil (40 moles of ethylene oxide) | 6.0 | | | 5.0 | | | 8.0 | 8.0 | 8.0 | 7.0 | | 6.0 |
| Ethoxylated nonylphenol (10 moles of ethylene oxide) | | | 7.0 | | 15.0 | 15.0 | 15.0 | | 15.0 | | | |
| Ethoxylated tributylphenol (10 moles of ethylene oxide) | | 6.0 | | | | 7.0 | | | | 3.0 | 5.0 | |
| Ethoxylated oleyl alcohol (15 moles of ethylene oxide) | | | | | 5.0 | | | 2.0 | 2.0 | | | 2.5 |
| Ethoxylated tridecyl alcohol (8 moles of ethylene oxide) | 15.0 | 15.0 | 15.0 | 15.0 | | | | 15.0 | | | | |

BIOLOGICAL EXAMPLES

In the following use Examples, the test plants were grown in pots in a greenhouse. The concentrates, diluted in water, were applied when the monocotyledonous plants—*Alopecurus myosuroides, Avena fatua* and *Triticum aestivum*—had reached the 3-4 leaf stage and the dicotyledenous plants—*Stellaria media* and *Chenopodium album*—had grown to a height of 5-10 cm.

After 4 weeks, the action (damage) was rated. The degree of action found is compared with the expected degree of action in the Tables.

The expected degree of action was calculated from the formula of S. R. Colby, Calculating synergistic and antagonistic response of herbicide combinations (Weeds 15 pages 20-22, 1967).

The Colby formula is:

$$E = X + Y - \frac{X \cdot Y}{100}$$

in which
X = % damage by herbicide A applied in an amount of x kg/ha,
Y = % damage by herbicide B applied in an amount of y kg/ha
E = the expected damage of herbicides A + B applied in an amount of X + Y kg/ha.

If the actual damage is greater than the calculated damage, the action of the combination is more than additive, i.e. a synergistic effect exists. In the case of treatment with the combinations, the action calculated from the above formula is given in parentheses.

TABLE

Combating of monocotyledonous and dicotyledonous weeds in wheat (*Triticium aestivum*)

| Active substance[1] | Dose[2] g of AS/ha | Damage in % to | | | | |
|---|---|---|---|---|---|---|
| | | Alopecurus myosuroides | Avena fatua | Stellaria media | Chenopodium album | Triticum aestivum |
| $A_1$ | 7.5 | 0 | 0 | 0 | 0 | 0 |
| | 15 | 0 | 11 | 0 | 0 | 0 |
| | 22.5 | 0 | 33 | 0 | 0 | 0 |
| | 30 | 27 | 45 | 0 | 0 | 0 |
| | 37.5 | 41 | 58 | 0 | 0 | 0 |
| | 45 | 52 | 63 | 0 | 0 | 0 |
| | 75 | 65 | 88 | 0 | 0 | 0 |
| | 150 | 87 | 96 | 0 | 0 | 0 |
| $A_2$ | 37.5 | 0 | 0 | 0 | 0 | 0 |
| | 75 | 0 | 0 | 0 | 0 | 0 |
| | 112.5 | 0 | 10 | 0 | 0 | 0 |
| | 150 | 10 | 15 | 0 | 0 | 0 |
| | 187.5 | 15 | 38 | 0 | 0 | 0 |
| | 225 | 23 | 50 | 0 | 0 | 0 |
| | 375 | 38 | 65 | 0 | 0 | 0 |
| | 750 | 60 | 90 | 0 | 0 | 0 |
| $B_1$ | 7.5 | 0 | 0 | 0 | 0 | 0 |
| | 15 | 0 | 0 | 0 | 7 | 0 |
| | 22.5 | 0 | 0 | 0 | 22 | 0 |
| | 30 | 0 | 0 | 0 | 38 | 0 |
| | 37.5 | 0 | 0 | 0 | 51 | 0 |
| | 45 | 0 | 0 | 7 | 67 | 0 |
| | 75 | 10 | 0 | 13 | 80 | 0 |
| | 150 | 33 | 0 | 30 | 92 | 0 |
| $B_2$ | 7.5 | 0 | 0 | 20 | 0 | 0 |
| | 15 | 0 | 0 | 25 | 0 | 0 |
| | 22.5 | 0 | 0 | 27 | 25 | 0 |
| | 30 | 0 | 0 | 31 | 40 | 0 |
| | 37.5 | 0 | 0 | 37 | 45 | 0 |
| | 45 | 0 | 0 | 42 | 52 | 0 |
| | 75 | 0 | 0 | 53 | 65 | 0 |
| | 150 | 0 | 0 | 55 | 78 | 0 |
| $C_1$ | 7.5 | 0 | 0 | 20 | 0 | 0 |
| | 15 | 0 | 0 | 40 | 0 | 0 |
| | 22.5 | 0 | 0 | 52 | 0 | 0 |
| | 30 | 0 | 0 | 60 | 0 | 0 |

TABLE-continued

Combating of monocotyledonous and dicotyledonous weeds in wheat (*Triticium aestivum*)

| | Dose[2] g of AS/ha | Alopecurus myosuroides | Avena fatua | Stellaria media | Chenopodium album | Triticum aestivum |
|---|---|---|---|---|---|---|
| | 37.5 | 0 | 0 | 70 | 0 | 0 |
| | 45 | 0 | 0 | 75 | 0 | 0 |
| | 75 | 14 | 7 | 86 | 27 | 0 |
| | 150 | 24 | 7 | 100 | 40 | 0 |
| Active substance combination | | | | | | |
| $A_1 + C_1$ | 22.5 + 22.5 | — | — | 82 (52) | — | 0 |
| | 45 + 45 | 87 (52) | 82 (63) | 90 (75) | — | 0 |
| | 7.5 + 37.5 | — | — | 87 (70) | — | 0 |
| | 15 + 75 | — | — | 99 (86) | — | 0 |
| | 30 + 150 | 72 (45) | 75 (49) | — | 68 (40) | 0 |
| | 37.5 + 7.5 | 78 (41) | 82 (58) | 68 (20) | — | 0 |
| | 75 + 15 | 90 (65) | 95 (88) | 77 (40) | — | 0 |
| | 150 + 30 | 99 (87) | — | 85 (60) | — | 0 |
| $A_2 + C_1$ | 75 + 75 | — | — | 93 (86) | — | 0 |
| | 150 + 150 | 48 (32) | 55 (21) | — | 73 (40) | 0 |
| | 75 + 15 | — | — | 57 (40) | — | 0 |
| | 112.5 + 22.5 | — | — | 68 (52) | — | 0 |
| | 150 + 30 | — | — | 84 (60) | — | 0 |
| | 150 + 15 | — | — | 62 (40) | — | 0 |
| | 225 + 22.5 | — | 63 (50) | 78 (52) | — | 0 |
| | 375 + 37.5 | 59 (38) | 79 (65) | 92 (70) | — | 0 |
| | 750 + 75 | 87 (66) | 100 (91) | 100 (86) | 62 (27) | 0 |
| $A_1 + B_1$ | 22.5 + 22.5 | — | — | — | 59 (22) | 0 |
| | 45 + 45 | 70 (52) | 80 (63) | — | 91 (67) | 0 |
| | 7.5 + 37.5 | — | — | — | 83 (61) | 0 |
| | 15 + 75 | — | — | — | 100 (80) | 0 |
| | 30 + 150 | 69 (52) | 78 (45) | — | 100 (92) | 0 |
| | 37.5 + 7.5 | 65 (41) | 89 (58) | — | — | 0 |
| | 75 + 15 | 87 (65) | 93 (88) | — | — | 0 |
| | 150 + 30 | 95 (87) | — | — | 78 (38) | 0 |
| $A_1 + B_2$ | 22.5 + 22.5 | — | — | — | 64 (25) | 0 |
| | 45 + 45 | 73 (52) | 87 (63) | 53 (42) | 82 (52) | 0 |
| | 7.5 + 37.5 | — | — | — | 80 (45) | 0 |
| | 15 + 75 | — | — | — | 99 (65) | 0 |
| | 30 + 150 | 65 (27) | 78 (45) | 79 (55) | 100 (78) | 0 |
| | 37.5 + 7.5 | 67 (41) | 85 (58) | — | — | 0 |
| | 75 + 15 | 80 (65) | 93 (88) | — | — | 0 |
| | 150 + 30 | 92 (87) | — | — | 82 (40) | 0 |

[1] for the meanings of $A_1$, $A_2$, $B_1$, $B_2$ and $C_1$, see the descriptive section, page 3
[2] AS = Active Substance

We claim:

1. A herbicidal composition consisting essentially of a herbicidally effective amount of a combination of compound of the formula (A)

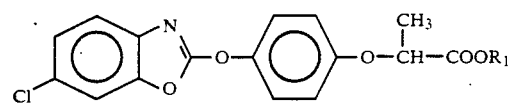 (A)

wherein
 $R_1$ is H, methyl, ethyl or an alkali metal cation and a compound of the formula (B)

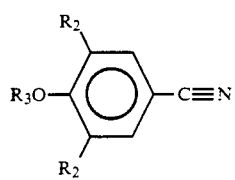 (B)

wherein
 $R_2$ is bromine or iodine and
 $R_3$ is octanoyl or an alkali metal cation wherein the ratio by weight of A:B is from 1:5 to 5:1.

2. A herbicidal composition as in claim 1, wherein compound (A) is ethyl alpha[4-(6-chlorobenzoxazolyl-oxy)-phenoxy]-propionate.

3. A method for combatting grassy weeds in cultivated areas of crops of cereals, which comprises applying an effective amount of a herbicidal composition as in claim 1 to said weed or to said cultivated areas.

4. A method as claimed in claim 3, wherein the crops are wheat plants.

5. A method for combatting grassy weeds in cultivated areas of wheat plants which comprises applying a herbicidally effective amount of a composition consisting essentially of the herbicide ethyl alpha[4-(6-chlorobenzoxazolyl-oxy)-phenoxy]-propionate (A1) in combination with a herbicide of formula (B)

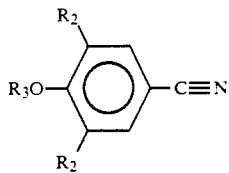

wherein

R$_2$ is bromine or iodine and

R$_3$ is octanoyl or an alkali metal cation wherein the ratio by weight of A:B is from 1:5 to 5:1.

6. A method as claimed in claim 5, wherein the grassy weed in *Avena fatua* or *Alopecurus myosuroides*.

7. A herbicidal composition as in claim 1, wherein the second component is the compound B in which R$_3$ is octanoyl.

8. The herbicidal composition as claimed in claim 1, wherein R$_2$ is bromine and R$_3$ is octanoyl.

9. The herbicidal composition as claimed in claim 1, wherein R$_2$ is iodine and R$_3$ is octanoyl.

10. The herbicidal composition as claimed in claim 2, wherein R$_2$ is bromine and R$_3$ is octanoyl.

11. The herbicidal composition as claimed in claim 2, wherein R$_2$ is iodine and R$_3$ is octanoyl.

12. The method as claimed in claim 5, wherein R$_2$ is bromine and R$_3$ is octanoyl.

13. The method as claimed in claim 5, wherein R$_2$ is iodine and R$_3$ is octanoyl.

14. The method as claimed in claim 12, wherein R$_1$ is ethyl.

15. The method as claimed in claim 13, wherein R$_1$ is ethyl.

* * * * *